United States Patent
Akamatsu et al.

(10) Patent No.: US 10,101,264 B2
(45) Date of Patent: Oct. 16, 2018

(54) MULTIPLE REFLECTION TYPE CELL AND ANALYZER

(71) Applicant: HORIBA, Ltd., Kyoto (JP)

(72) Inventors: Takeshi Akamatsu, Kyoto (JP);
Yoshiyuki Nakajima, Kyoto (JP)

(73) Assignee: Horiba Ltd., Kyoto (JP)

( * ) Notice: Subject to any disclaimer, the term of this patent is extended or adjusted under 35 U.S.C. 154(b) by 0 days.

(21) Appl. No.: 15/477,329

(22) Filed: Apr. 3, 2017

(65) Prior Publication Data

US 2017/0284929 A1 Oct. 5, 2017

(30) Foreign Application Priority Data

Apr. 1, 2016 (JP) ................. 2016-074604

(51) Int. Cl.
| | |
|---|---|
| *G01N 21/03* | (2006.01) |
| *G01N 21/3504* | (2014.01) |
| *G01N 33/00* | (2006.01) |
| G01N 21/35 | (2014.01) |

(52) U.S. Cl.
CPC ....... *G01N 21/0303* (2013.01); *G01N 21/031* (2013.01); *G01N 21/3504* (2013.01); *G01N 33/004* (2013.01); *G01N 33/0037* (2013.01); *G01N 2021/3595* (2013.01);
(Continued)

(58) Field of Classification Search
CPC ............... G01N 21/0303; G01N 21/03; G01N 21/3504; G01N 33/0037; G01N 33/004
See application file for complete search history.

(56) References Cited

U.S. PATENT DOCUMENTS

| 3,567,329 | A | 3/1971 | Willis et al. | |
|---|---|---|---|---|
| 2008/0111993 | A1* | 5/2008 | Miller | G01N 21/39 356/437 |
| 2016/0069797 | A1* | 3/2016 | Chanda | G01N 21/39 356/437 |

FOREIGN PATENT DOCUMENTS

| CN | 103884677 A | 6/2014 |
|---|---|---|
| DE | 102008044171 A1 | 6/2010 |

(Continued)

OTHER PUBLICATIONS

EESR dated Jun. 29, 2017 issued for European patent application No. 17 163 378.7, 13 pgs.

*Primary Examiner* — Hugh H Maupin
(74) *Attorney, Agent, or Firm* — Brooks Kushman P.C.

(57) ABSTRACT

This invention is a multiple reflection type cell that makes it possible to reduce a dead space resulting from a position adjusting mechanism and to adjust the light to a desired optical path length without complicating a structure. The multiple reflection type cell comprises a cell body where a cell chamber is formed, two or more reflecting members that are mounted on the cell body and whose reflecting surfaces locate in the cell chamber, and a position adjusting mechanism that adjusts a position of the reflecting member relative to the cell body. The cell body has a mounting part that communicates the cell chamber and the outside and on which the reflecting members are mounted. A seal member that seals a gap between the cell chamber and the outside of the cell body is arranged between the reflecting member mounted on the mounting part and the cell body so that the gap between the cell chamber and the outsider of the cell body is sealed by the seal member.

7 Claims, 4 Drawing Sheets

(52) U.S. Cl.
CPC ................ *G01N 2201/0227* (2013.01); *G01N 2201/0636* (2013.01); *Y02A 50/245* (2018.01)

(56) References Cited

FOREIGN PATENT DOCUMENTS

| | | |
|---|---|---|
| JP | 08-035926 A | 2/1996 |
| JP | 09-101257 A | 4/1997 |

\* cited by examiner

MULTIPLE REFLECTION TYPE CELL AND ANALYZER

CROSS-REFERENCE TO RELATED APPLICATION

This application claims priority to JP Application No. 2016-074604, filed Apr. 1, 2016, the disclosure of which is incorporated in its entirety by reference herein.

FIELD OF THE ART

This invention relates to a multiple reflection type cell that emits incident light outside after reflecting the light at multiple times and an analyzer that uses the multiple reflection type cell.

BACKGROUND ART

Absorption spectrophotometry of a measurement object gas using, for example, FTIR (Fourier Transformation Infrared Spectrometer) uses a multiple reflection type cell of a white type having multiple reflecting surfaces in order to lengthen an optical path length of light passing the measurement object gas while shortening a cell length of a cell chamber into which the measurement object gas is introduced (refer to patent document 1, 2).

For this multiple reflection type cell, a reflecting member having the reflecting surface is adjusted by a position adjusting mechanism such as a set screw or a drawing thread in order to obtain a desired optical path length. Ordinarily, the position adjusting mechanism is housed in a cell chamber in order to simplify a cell structure. With this structure, it is necessary to take an inner volume of the cell chamber large in order to house the position adjusting mechanism.

In case of measuring a time change of a component of the measurement object gas by the use of the multiple reflection type cell, it is required the responsiveness should be improved by shortening time to replace the introduced measurement object gas as much as possible and decreasing the inner volume of the cell chamber.

In order to attain this object, the multiple reflection type cell described in the patent document 1 has a structure wherein a block body is arranged in a dead space of the cell chamber so as to decrease the inner volume of the cell chamber.

However, this multiple reflection type cell reduces the dead space of a lateral side (a peripheral part locating at a position orthogonal to the optical path) of the optical path of the multiple reflection, and does not reduce a dead space resulting from the position adjusting mechanism of the reflecting member. In addition, since this structure requires a block body provided separately, not only the structure becomes complicated but also a dead space where the measurement sample gas resides is formed in a gap between the block body and the inside surface of the cell chamber. Furthermore, the structure wherein a dead space resulting from the position adjusting mechanism is formed or the block body is provided becomes an obstacle to downside the multiple reflecting type cell.

A multiple reflecting type cell described in the patent document 2 has a gas container into which the sample is introduced and three reflecting members arranged in both sides of the gas container, and the sample gas and the reflecting members are separated by a window of the gas container. With this structure, it is possible to exclude the dead space resulting from the position adjusting mechanism.

However, with this structure, it is necessary to provide an additional structure (concretely, a brewster window) in order to reduce reflection of the light when the light passes a window of the gas container. In addition, since the sample gas and the reflecting member are separately arranged, not only the optical path length between the sample gas and the reflecting member becomes wasteful but also whole of the cell increases in size to gain a desired optical path length.

PRIOR ART DOCUMENT

Patent Document

Patent document 1: Japanese Unexamined Patent Application Publication No. 9-101257
Patent document 2: Japanese Unexamined Patent Application Publication No. 8-35926

DISCLOSURE OF THE INVENTION

Problems to be Solved by the Invention

The present claimed invention intends to solve all of the problems and a main object of this invention is to make it possible to reduce a dead space resulting from a position adjusting mechanism and to adjust the light to have a desired optical path length without complicating a structure.

Means to Solve the Problems

More specifically, the multiple reflection type cell in accordance with this invention is a multiple reflection type cell that reflects incident light at multiple times and subsequently emits the reflected light to the outside, comprises a cell body where a cell chamber into which a sample is introduced is formed, two or more reflecting members that are mounted on the cell body and whose reflecting surfaces locate in the cell chamber and a position adjusting mechanism that adjusts a position of the reflecting member relative to the cell body. The cell body has a mounting surface that communicates the cell chamber and the outside and on which the reflecting members are mounted, a seal member that seals a gap between the cell chamber and the outside of the cell body is arranged between the reflecting member mounted on the mounting part and the cell body, and the position adjusting mechanism is arranged outside of the cell chamber.

In accordance with the analyzer of this embodiment having this structure, since the gap between the cell chamber and the outside of the cell body is sealed by the seal member arranged between the second reflecting member and the cell body, and the position adjusting mechanism is arranged outside of the cell chamber, it is possible to eliminate a dead space inside of the cell chamber generated by arranging the position adjusting mechanism inside of the cell chamber and to adjust the light to have a desired optical path length. With this structure, it is possible to shorten permutation time of the sample as much as possible by reducing an internal volume of the cell chamber and to improve responsiveness.

In addition, since the reflecting surface of the reflecting member locates inside of the cell chamber, there is no need of providing a window or the like in front of the reflecting surface and a structure to reduce reflection of the window, and it is possible to make use of whole of the space between two reflecting surfaces each of which mutually faces as the optical path length. Furthermore, since no window is required between the sample and the reflecting surface, there is no worry about enlarging whole of the cell in order to obtain the desired optical path length.

If a moving amount of the reflecting member adjusted by the position adjusting mechanism exceeds a movable range by making use of the seal member, it is not possible to secure airtightness of the cell chamber.

In order to preferably solve this problem, it is preferable that the position adjusting mechanism adjusts the position of the reflecting member within a movable range by the seal member.

It is preferable that the mounting part is arranged to incline along a mounting angle of the reflecting member to the cell body.

In accordance with this structure, it is possible to adjust a most part of the mounting angle of the reflecting member by the inclination of the mounting part and to adjust the reflecting member minutely by the position adjusting mechanism. As a result of this, it becomes possible and easy to adjust the position of the reflecting member within a movable range by the seal member.

As a concrete embodiment of the multiple reflecting type cell, conceived is a structure wherein three reflecting members are provided and a first reflecting member as being one of the reflecting members is arranged to face to second reflecting members as being the remaining two reflecting members. Then, the above-mentioned two second reflecting members are arranged symmetrically with a surface containing an optical axis of the first reflecting member and an optical axis of each of the second reflecting members is inclined to a direction to approach toward the first reflecting member.

In accordance with this structure, it becomes especially difficult to position the second reflecting member whose optical axis inclines. As this result, it is preferable that a position of the second reflecting member is arranged adjustably by the position adjusting mechanism.

It is necessary to provide the cell body with an incident window through which the light enters from outside and an emitting window that reflects the light. If the cell body is provided with the incident window and the emitting window in the second reflecting member side, the position adjusting mechanism makes it difficult to arrange a window at a desired position. Then as a structure to easily provide the cell body with the incident window and the emitting window it is preferable that the first reflecting member is fixed to the cell body and the incident window that enters the light to the first reflecting member side and the emitting window that emits the light are arranged in the cell body.

In order to simplify the structure of the reflecting member, the mounting part and the seal member, it is preferable that the reflecting member is in a cylindrical shape having the reflecting surface on its distal end surface, the mounting part has an inside peripheral surface whose cross-section is a circle to face to an outside peripheral surface of the reflecting member, and the seal member airtightly seals a gap between the outside peripheral surface of the reflecting member and the inside peripheral surface of the mounting part.

For example, in order to enable the positioning of the reflecting member after the multiple reflecting type cell is assembled, it is preferable that the position adjusting mechanism is arranged to face to the outside of the cell body.

Effect of the Invention

In accordance with the present claimed invention having the above-mentioned structure, since the gap between the cell chamber and the outside of the cell body is sealed by the seal member arranged between the second reflecting member and the cell body, and the position adjusting mechanism is arranged outside of the cell chamber, it is possible to eliminate a dead space inside of the cell chamber generated by arranging the position adjusting mechanism inside of the cell chamber and to adjust the light to have a desired optical path length.

BEST MODES OF EMBODYING THE INVENTION

One embodiment of an analyzer using a multiple reflection type cell in accordance with this invention will be explained with reference to drawings.

The analyzer 100 in this embodiment is an exhaust gas analyzer that measures a concentration of each of multiple components contained in an exhaust gas as being a sample gas discharged from an internal combustion engine such as an automobile as a time-series data.

Figure 1:
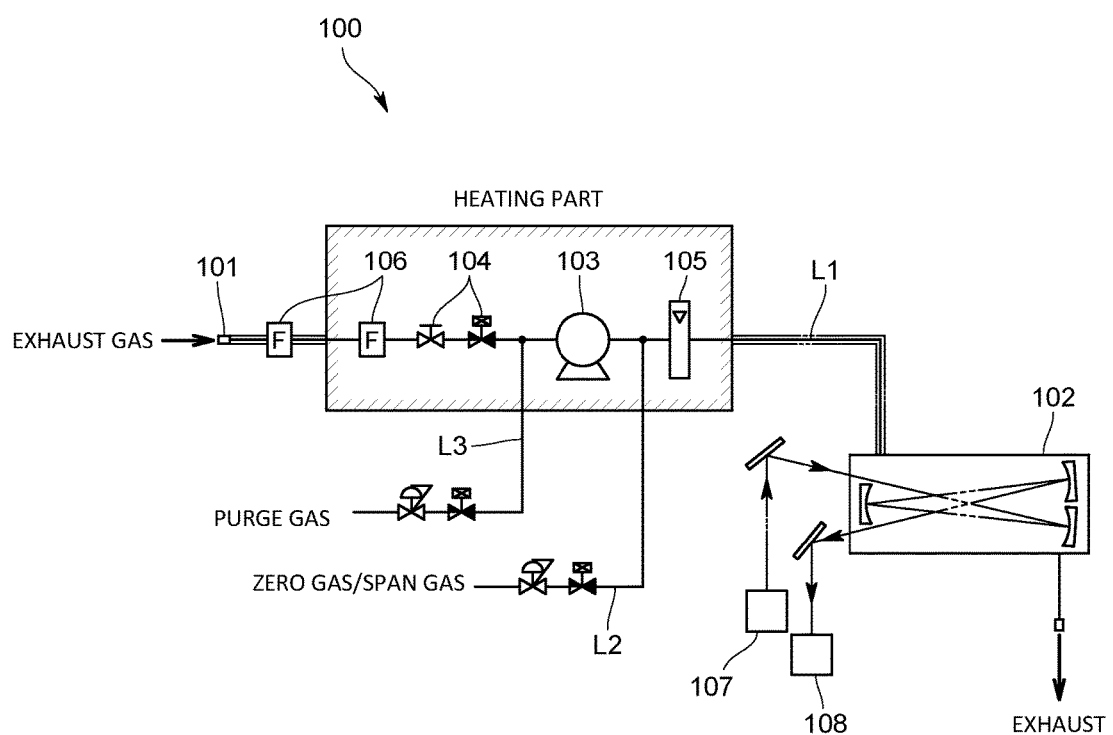
FIG. 1 is a pattern view showing a structure of an analyzer of this embodiment.

Concretely, as shown in FIG. 1, the analyzer 100 takes a part or all of the exhaust gas discharged from, for example, a tail pipe of the automobile by the a sample sampling part 101, introduces the exhaust gas sampled by the sample sampling part 101 into a multiple reflection type cell 102 without diluting the exhaust gas and measures each concentration of the multiple component such as carbon dioxide ($CO_2$), nitrogen oxide ($NO_X$) or the like in the exhaust gas by the use of FTIR method.

In addition, for the analyzer 100, a pump 103 to introduce the exhaust gas into the multiple reflection type cell 102, a valve 104 to adjust a flow rate of the exhaust gas, a flow meter 105 to measure the flow rate of the exhaust gas and a filter 106 to remove dust in the exhaust gas are arranged in an exhaust gas line L1 on which the multiple reflection type cell 102 is provided. The pump 103 may be arranged upstream or downstream of the multiple reflection type cell 102. In addition, a reference gas supply line L2 to supply zero gas to correct a photoelectric detector 108 and span gas to the multiple reflection type cell 102 and a purge gas line L3 to clean the exhaust gas line L1 or the multiple reflection type cell 102 are connected to the exhaust gas line L1 or the multiple reflection type cell 102.

Furthermore, the analyzer 100 comprises a light source 107 to irradiate infrared light to the multiple reflection type cell 102 and a light detector 108 to detect an intensity of the light that passes the multiple reflection type cell 102 and that is irradiated from the multiple reflection type cell 102. In addition, the analyzer 100 calculates an infrared absorption spectrum of the exhaust gas by the use of a light intensity signal obtained by the light detector 108 and calculates the concentration of multiple components based on the infrared absorption spectrum.

Next, the multiple reflection type cell 102 will be explained in detail with reference to FIG. 2~FIG. 4.

Figure 2:
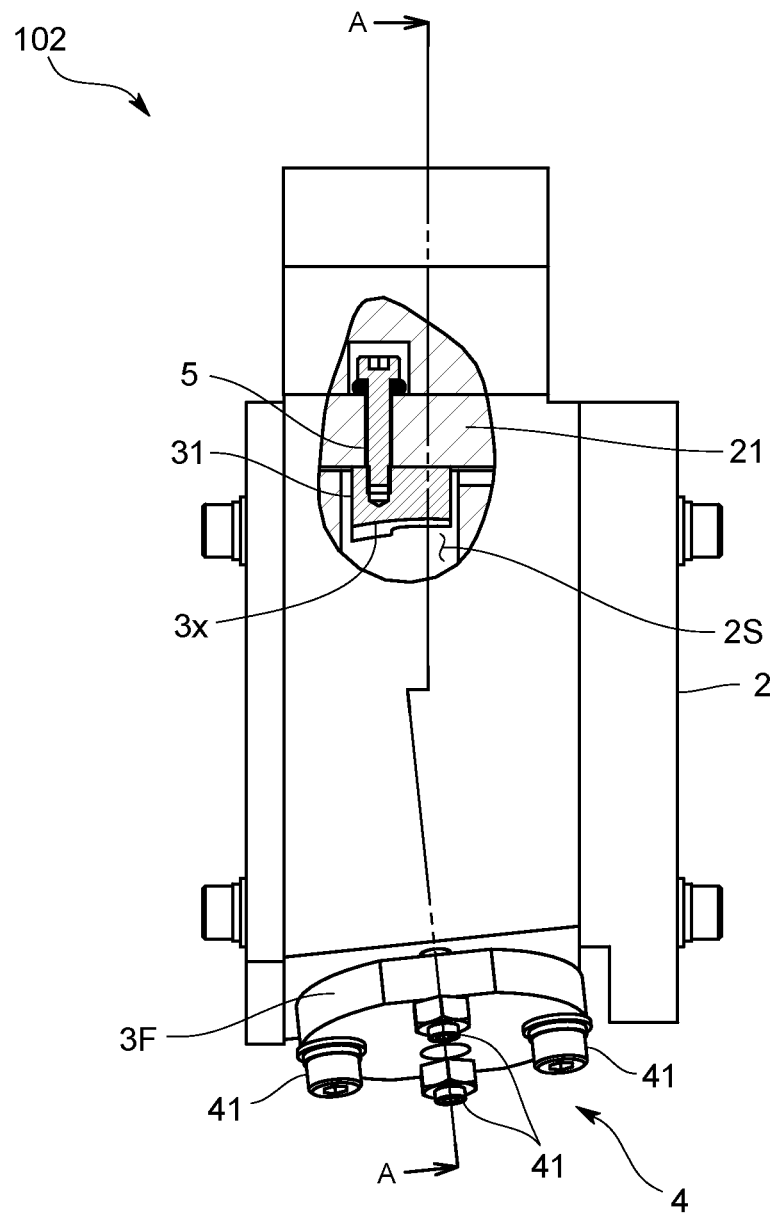
FIG. 2 is a side view showing a partial cross-sectional view of a multiple reflection type cell in this embodiment.
Figure 3:
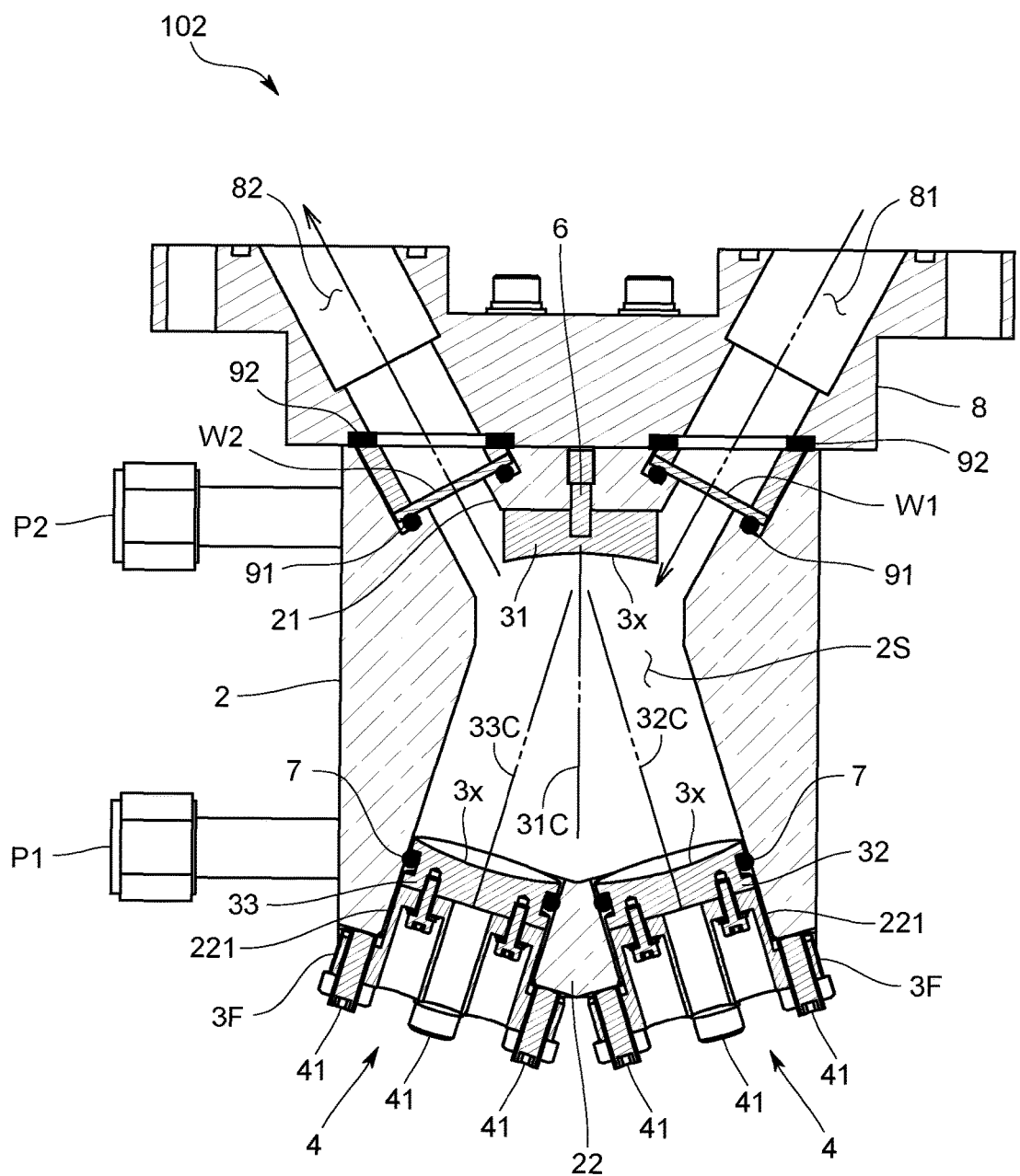
FIG. 3 is a cross-sectional view taken along a line A-A in this embodiment.

The multiple reflection type cell 102 comprises, especially as shown in FIG. 2 and FIG. 3, a cell body 2 where a cell chamber 2S into which the exhaust gas is introduced is formed, three reflecting members 31, 32, 33 that are mounted on the cell body 2 and whose reflecting surfaces 3x locate in the cell chamber 2S and a position adjusting mechanism 4 that adjusts positions of the reflecting members 32, 33 relative to the cell body 2. The cell body 2 is provided with an introducing port P1 to introduce the exhaust gas and a discharging port P2 to discharge the exhaust gas (refer to FIG. 3).

Especially as shown in FIG. 3, the cell body 2 is so arranged that the first reflecting member 31 as being one of the reflecting members faces to the second reflecting members 32, 3 as being remaining two reflecting members. The two second reflecting member 32, 33 are arranged symmetrically with a surface containing an optical axis 31C of the first reflecting member 31 and an optical axis 32C, 33C of each of the second reflecting members 32, 33 is inclined to a direction to approach toward the first reflecting member 31.

The first reflecting member 31 is in a plate shape at a distal end of which a reflecting surface 3x is forms. The first reflecting member 31 is fixed to an inner surface of a first side wall part 21 that forms the cell chamber 2S that is formed inside of the cell body 2 by a screw 5 (refer to FIG. 2). Concretely, the first reflecting member 31 is screw-fixed through a through bore formed on the first side wall part 21 from the outside of the first side wall part 21. A rear end surface of the first reflecting member 31 is tightly attached to an inner surface of the first side wall part 21. The first reflecting member 31 is positioned relative to the cell body 2 by a parallel pin 6 (refer to FIG. 3) inserted into a rear surface of the first reflecting member 31 and the first side wall part 21 or a convexoconcave structure formed between the rear surface of the first reflecting member 31 and the first side wall part 21.

Meanwhile, each of the two second reflecting members 32, 33 is mounted on a mounting part 221 arranged on a second side wall part 22 that faces to the first side wall part 21 of the cell body 2. The mounting part 221 is a through bore that communicates the cell chamber 2S and the outside of the cell body 2 and is arranged on each of the two second reflecting members 32, 33 respectively. In addition, the mounting part 221 roughly determines an angle of mounting the second reflecting member 32, 33 relative to the cell body 2, and is inclined along the angle.

The second reflecting member 32, 33 is in a cylindrical shape whose distal end surface formed is a reflecting surface 3x. In correspondence to this, the mounting part 221 has an inside peripheral surface 221p whose cross sectional surface is a circular to face to an outside peripheral surface 33p of the second reflecting member 32, 33 (refer to FIG. 4).

Figure 4:
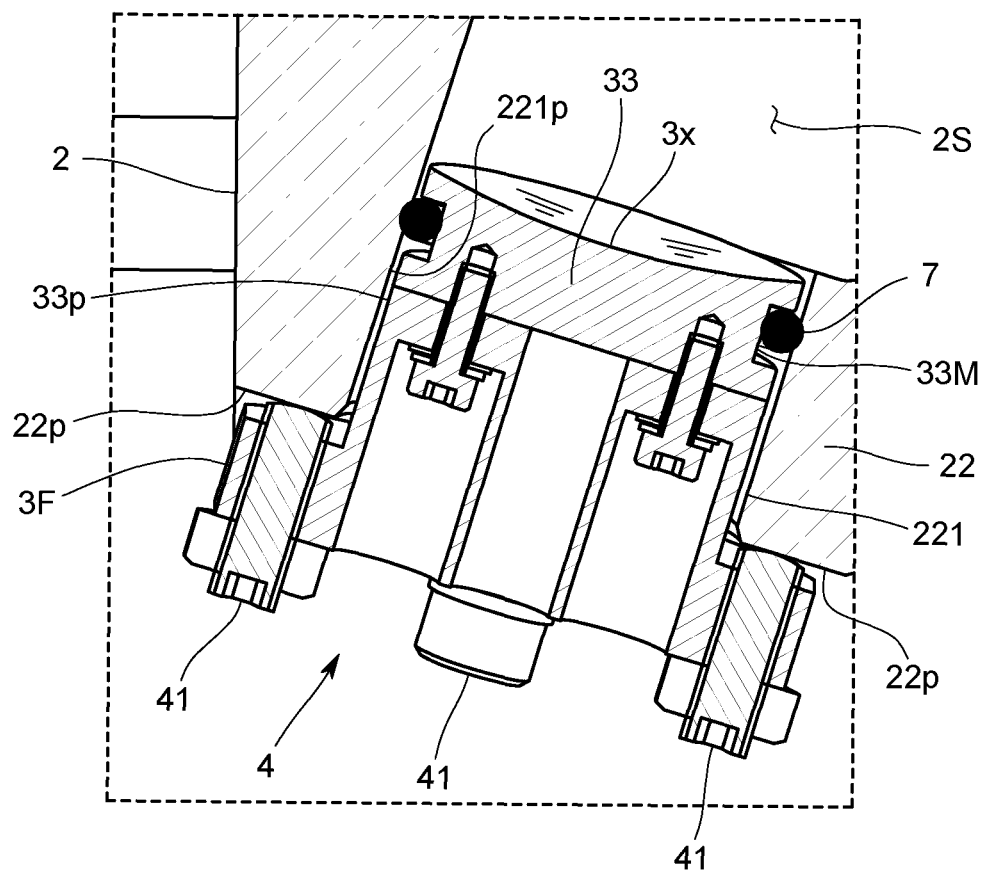
FIG. 4 is an enlarged cross-sectional view showing a positional relationship between a cell body, a second reflecting member, a seal member and a position adjusting mechanism.

As shown in FIG. 3 and FIG. 4, a seal member 7 is arranged between the second reflecting member 32, 33 that is mounted on the mounting part 221 by being inserted into the mounting part 221 and the cell body 2. The seal member 7 is made of an elastic material to fill a gap between the second reflecting member 32, 33 and the cell body 2 and is, for example, an O-ring. The second reflecting member 32, 33 is mounted on the mounting part 221 of the cell body 2 without rattling.

A peripheral structure of the seal member 7 in a side of the second reflecting member 33 will be explained in detail with reference to FIG. 4. A structure of a side of the second reflecting member 32 is the same as that of a side of the second reflecting member 33.

The seal member 7 airtightly seals a gap between the outside peripheral surface 33p of the second reflecting member 33 and the inside peripheral surface 221p of the mounting part 221. The seal member 7 is so arranged that a part of the seal member 7 locates at an annular concave groove 33M formed on the outside peripheral surface at a distal end part of the second reflecting member 33. The seal member 7 arranged on the concave groove 33M airtightly seals the cell chamber 2S at the distal end part side of the second reflecting member 32, 33. In addition, the second reflecting member 32, 33 is held at the mounting part 221 by the seal member 7.

In order to reduce a dead space between the outside peripheral surface 33p of the second reflecting member 33 and the inside peripheral surface 221p of the mounting part 221 on the cell chamber 2S side from the seal member 7 as much as possible, it is preferable to form the concave groove 3M near the reflecting surface 3x of the second reflecting member 33.

The position of the second reflecting member 32, 33 that is mounted on the mounting part 221 through the seal member 7 can be adjusted by the position adjusting mechanism 4.

Concretely, the position adjusting mechanism 4 finely adjusts the position of the second reflecting member 32, 33 relative to the cell body 2 by making an abutting contact with the cell body 2. The position adjusting mechanism 4 is arranged to be reciprocally movable relative to the second reflecting member 32, 33 and uses an adjusting screw that makes an abutting contact with a facing surface of the cell body 2.

The adjusting screw 41 is arranged on a flange part 3F provided on a rear end part of the second reflecting member 32, 33. The flange part 3F is arranged to face to an outside surface 22p of the second side wall part 22 of the cell body 2.

The adjusting screw 41 is screwed to a female screw hole that penetrates the flange part 3F in its thickness direction. In this embodiment, the adjusting screw 41 is arranged at four positions respectively at even intervals along a center axis of the second reflecting member 32, 33 on the circular flange part 3F. A distal end part of the adjusting screw 41 makes an abutting contact with an outside surface 22p of the second side wall part 22. In addition, since the adjusting screw 41 is arranged on the flange part 3F that locates outside of the cell boy 2, the position adjusting mechanism 4 locates to face to the outside of the cell body 2.

In accordance with the position adjusting mechanism 4 having this structure, the position of the second reflecting member 32, 33 is adjusted relative to the mounting part 221 of the cell body 2. For example, a position of the second reflecting member 32, 33 along a direction of the optical axis 32C, 33C is adjusted relatively to the cell body 2 and a direction of the optical axis 32C, 33C is also adjusted by adjusting a projecting amount of each of the four adjusting screws 41 from the flange part 3F to the cell body 2. In addition to the adjusting screw 41 that makes an abutting contact with the outside surface 22p, the adjusting screw 41 may be an adjusting screw that adjusts the position of the second reflecting member 32, 33 by threadably engaging the female screw hole formed on the second side wall part 22 and adjusting a threaded amount of the adjusting screw 41 to the female screw bore.

A moving amount of the second reflecting member 32, 33 by the position adjusting mechanism 4 is set to be within a movable range by the O-ring 7. The movable range by the O-ring 7 is a range that has no influence on the measurement. More specifically, the moving amount of the second reflecting member 32, 33 by the position adjusting mechanism 4 is set to be within a range wherein sealing by the O-ring 7 can be secured to a certain degree that does not have an influence on the measurement. The allowable sealing amount of the O-ring 7 is an amount of the range wherein a sealing characteristic of the O-ring 7 can be secured, and is, for example, an amount wherein a crush rate (equal to a crush amount □/O-ring diameter (W)) of each part along a circumferential direction of the O-ring 7 falls in a range of 8~30%. A backlash amount of the second reflecting member 32, 33 to the mounting part 221 is set so as not to interfere the position adjustment by the position adjusting mechanism 4.

In addition, for the multiple reflection type cell 102 of this embodiment, an incident window W1 to introduce the light into the inside of the cell chamber 2S and an emitting window W2 to emit the light to the outside of the cell chamber 2S are arranged on the first side will part 21 to which the first reflecting member 31 is fixed. Concretely, the incident window W1 and the emitting window W2 are arranged in the opposite positions in the both sides of the first reflecting member 31 along the arrangement direction of the second reflecting member 32, 33.

The multiple reflection type cell 102 in this embodiment is so configured that the light that enters from the incident window W1 enters into the second reflecting member 33 locating farther viewed from the incident window W1. In other words, the incident window W1 is arranged to incline so as to face to the second reflecting member 33 locating farther. Meanwhile, the emitting window W2 is arranged to incline so as to face to the second reflecting member 32 locating farther viewed from the emitting window W2. The incident window W1 may be arranged to face to the second reflecting member 32 locating closer and the emitting window W2 may be arranged to face to the second reflecting member 33 locating closer.

The multiple reflection type cell 102 in this embodiment is so configured that a flange member 8 for mounting the multiple reflection type cell 102 on a member locating outside is fixed to the outside surface of the first side wall part 21 of the cell body 2 by a screw. An introducing path 81 to introduce the light from the light source 107 into the incident window W1 and a discharging path 82 to introduce the light emitted from the emitting window W2 into a light detector 108 are formed on the flange member 8. In addition, each of a gap between the cell body 2 and the incident window W1, a gap between the cell body 2 and the emitting window W2 and a gap between the cell body 2 and the flange member 8 is sealed by a seal member 91, 92 such as, for example, an O-ring. Either one of the gaps may be sealed.

In accordance with the analyzer 100 of this embodiment having this structure, since the gap between the cell chamber 2S and the outside of the cell body 2 is sealed by the seal member 7 arranged between the second reflecting member 32, 33 and the cell body 2, and the position adjusting mechanism 4 is arranged outside of the cell chamber 2S, it is possible to eliminate a dead space inside of the cell chamber 2S formed by arranging the position adjusting mechanism 4 inside of the cell chamber 2S and to adjust the light to have a desired optical path length. With this structure, it is possible to shorten permutation time of the sample as much as possible by reducing an internal volume of the cell chamber 2S and to improve responsiveness.

In addition, since the reflecting surface 3x of the reflecting member 31~33 locates inside of the cell chamber 2S, there is no need of providing a window or the like in front of the reflecting surface 3x. Then, no structure is required to reduce reflection of the window and it is possible to make use of whole of the space between two reflecting surfaces 3x, 3x each of which mutually faces as the optical path length. Furthermore, since no window is required between the exhaust gas and the reflecting surface 3x, it is possible to downsize whole of the cell in order to obtain the desired optical path length.

The present claimed invention is not limited to the above-mentioned embodiment.

For example, in the above-mentioned embodiment, two second reflecting members 32 and 33 are adjustable by the position adjusting mechanism 4, however, the first reflecting member 31 may be adjustable by the position adjusting mechanism 4, and at least one of the reflecting members 31, 32, 33 may be adjustable by the position adjusting mechanism 4.

In addition, three reflecting members 31, 32, 33 are used for reflection at multiple times in the above-mentioned embodiment, however, two reflecting members or more than four reflecting members may be used for reflection at multiple times.

Furthermore, the light that enters from the incident window W1 enters into the second reflecting member 33 locating farther viewed from the incident window W1 in the above-mentioned embodiment, however, the light may enter into the second reflecting member 32 locating closer. With this structure also, the light reflects at multiple times between the first reflecting member 31 and the second reflecting member 32, 33 and is emitted from the discharging window W21.

Furthermore, the exhaust gas sampled by the sample sampling part 101 is introduced into the multiple reflection type cell 102 without diluting the exhaust gas in the above-mentioned embodiment, however, the exhaust gas may be diluted by the use of a dilution gas such as atmosphere and the diluted exhaust gas may be introduced into the multiple reflection type cell 102. The diluted exhaust gas is a gas with a predetermined ratio (a dilution ratio) of the exhaust gas and the dilution gas.

In addition, it is a matter of course that the present claimed invention is not limited to the above-mentioned embodiment and may be variously modified without departing from a spirit of the invention.

EXPLANATION OF CODES

100 . . . analyzer
102 . . . multiple reflection type cell
2 . . . cell body
221 . . . mounting part
2S . . . cell chamber
W1 . . . incident window
W2 . . . emitting window
31 . . . first reflecting member
31C . . . optical axis of first reflecting member
32 . . . second reflecting member
32C . . . optical axis of second reflecting member
33 . . . second reflecting member
33C . . . optical axis of second reflecting member
3x . . . reflecting surface
4 . . . position adjusting mechanism
7 . . . O ring (seal member)

What is claimed is:

1. A multiple reflection type cell that reflects incident light at multiple times and subsequently emits reflected light outside, comprising:
   a cell body where a cell chamber into which a sample is introduced is formed;
   two or more reflecting members that are mounted on the cell body and whose reflecting surfaces locate in the cell chamber, each of the reflecting members having the reflecting surface on a distal end surface; and
   a position adjusting mechanism arranged outside of the cell chamber and that adjusts a position of the reflecting members relative to the cell body, wherein
   the cell body has a mounting part that communicates the cell chamber and the outside and on which the reflecting members are mounted, the mounting part having an inside peripheral surface configured to face an outside peripheral surface of each of the reflecting members, and
   a seal member that fills and airtightly seals a gap between the outside peripheral surface of one of the reflecting members and the inside peripheral surface of the mounting part to form a seal between the cell chamber and an outside of the cell body.

2. The multiple reflection type cell described in claim 1, wherein
   the position adjusting mechanism adjusts the position of the one of the reflecting members within a movable range by the seal member.

3. The multiple reflection type cell described in claim 1, wherein
   the mounting part is arranged to incline along a mounting angle of the reflecting members to the cell body.

4. The multiple reflection type cell described in claim 1, wherein
   the two or more reflecting members include three reflecting members,
   one of the three reflecting members is arranged to face the other two of the three reflecting members,
   the other two of the three reflecting members are arranged symmetrically with a surface containing an optical axis of the one of the three reflecting members and an optical axis of each of the other two of the three reflecting members is inclined to a direction to approach toward the one of the three reflecting members, and
   the other two of the three reflecting members are arranged in a manner of position adjustable by the position adjusting mechanism.

5. The multiple reflection type cell described in claim 1, wherein
   each of the reflecting members is in a cylindrical shape, and
   a cross-section of the inside peripheral surface is a circle, and.

6. The multiple reflection type cell described in claim 1, wherein
   the position adjusting mechanism is arranged to face the outside of the cell body.

7. An analyzer comprising the multiple reflection type cell described in claim 1.

* * * * *